(12) United States Patent
Shirai et al.

(10) Patent No.: US 10,024,700 B2
(45) Date of Patent: Jul. 17, 2018

(54) FLUID ANALYSIS DEVICE

(71) Applicant: HORIBA STEC, Co., Ltd., Kyoto-shi, Kyoto (JP)

(72) Inventors: Takashi Shirai, Kyoto (JP); Hiroyuki Okano, Kyoto (JP)

(73) Assignee: HORIBA STEC, CO., LTD., Kyoto-shi, Kyoto (JP)

(*) Notice: Subject to any disclaimer, the term of this patent is extended or adjusted under 35 U.S.C. 154(b) by 179 days.

(21) Appl. No.: 14/894,306

(22) PCT Filed: Aug. 22, 2014

(86) PCT No.: PCT/JP2014/071974
§ 371 (c)(1),
(2) Date: Nov. 25, 2015

(87) PCT Pub. No.: WO2015/029890
PCT Pub. Date: Mar. 5, 2015

(65) Prior Publication Data
US 2016/0131511 A1    May 12, 2016

(30) Foreign Application Priority Data
Aug. 28, 2013 (JP) .................. 2013-177385

(51) Int. Cl.
*G01F 1/69* (2006.01)
*G05D 7/06* (2006.01)
(Continued)

(52) U.S. Cl.
CPC ............... *G01F 1/69* (2013.01); *G01F 1/696* (2013.01); *G01N 25/18* (2013.01); *G05D 7/0635* (2013.01)

(58) Field of Classification Search
CPC ....... G01N 25/005; F02D 41/18; E21B 47/09; G01F 1/69; G01F 1/06
See application file for complete search history.

(56) References Cited

U.S. PATENT DOCUMENTS 7,275,426 B2 * 10/2007 Lahti .................. F02D 37/02
 73/114.32
7,430,903 B2 * 10/2008 Ramos .................. E21B 47/09
 374/E11.015
(Continued)

FOREIGN PATENT DOCUMENTS

| CN | 1156821 A | 8/1997 |
| CN | 1443300 A | 9/2003 |

(Continued)

OTHER PUBLICATIONS

ISA Japanese Patent Office, International Search Report Issued in Application No. PCT/JP2014/071974, dated Dec. 2, 2014, WIPO, 4 pages.
(Continued)

*Primary Examiner* — Jewel V Dowtin
(74) *Attorney, Agent, or Firm* — Alleman Hall Creasman & Tuttle LLP

(57) ABSTRACT

The present invention is configured to, on the basis of an upstream side parameter having a value that is related to a change rate of an upstream side voltage when a flow rate of measuring target fluid changes, and a downstream side parameter having a value that is related to a change rate of a downstream side voltage when the flow rate of the measuring target fluid changes, calculate a fluid-specific value exhibiting a specific value depending on the thermal conductivity of the fluid.

11 Claims, 9 Drawing Sheets

(51) Int. Cl.
*G01N 25/18* (2006.01)
*G01F 1/696* (2006.01)

(56) References Cited

U.S. PATENT DOCUMENTS 8,606,486 B2 \* 12/2013 Hammond .............. F02D 41/18
  701/103
2012/0191381 A1 7/2012 Takakura et al.
2016/0334349 A1\* 11/2016 Lotters ................. G01N 25/005

FOREIGN PATENT DOCUMENTS

| | | |
|---|---|---|
| CN | 1474165 A | 2/2004 |
| CN | 101351704 A | 1/2009 |
| CN | 102057263 A | 5/2011 |
| CN | 103424261 A | 12/2013 |
| CN | 204286519 U | 4/2015 |
| JP | H01227016 A | 9/1989 |
| JP | H05149767 A | 6/1993 |
| JP | 2000292235 A | 10/2000 |
| JP | 2002543385 A | 12/2002 |
| JP | 2003106886 A | 4/2003 |
| JP | 2005527819 A1 | 9/2005 |
| JP | 3726261 B | 12/2005 |
| JP | 2011209152 A | 10/2011 |
| JP | 2013134231 A | 7/2013 |
| WO | 0065343 A1 | 11/2000 |
| WO | 03100391 A1 | 12/2003 |
| WO | 2011040327 A1 | 4/2011 |

OTHER PUBLICATIONS

State Intellectual Property Office of the People's Republic of China, Office Action Issued in Application No. 201480030199.0, dated Apr. 17, 2018, 7 pages.

\* cited by examiner

FLUID ANALYSIS DEVICE

TECHNICAL FIELD

The present invention relates to a fluid analysis device that includes two electrical resistive elements in a flow path through which measuring target fluid flows, and on the basis of voltages applied in order to make the electrical resistive elements generate heat, analyzes the flow rate, type, physical property, and the like of the measuring target fluid.

BACKGROUND ART

For example, gases used for a semiconductor process include numbers of corrosive gases (such as $BCl_2$, $Cl_2$, HCl, and $ClF_3$) and reactive gases ($SiH_4$ and $B_2H_6$), and in the case of measuring the flow rate of such gas, a thermal flowmeter that can indirectly measure the flow rate without the need to bring a sensor terminal or the like into direct contact with the gas may be used.

The thermal flowmeter is one including: a fluid resistor that is arranged in a main flow path through which the gas flows; a narrow tube that connects between the upstream and downstream sides of the laminar flow element as a bypass and forms a sensor flow path through which the gas flows at a flow rate having a predetermined ratio with respect to the main flow path; and two electrical resistive elements that are provided on the upstream and downstream sides on the outer surface of the narrow tube. In addition, applied voltages are controlled so as to make the temperatures of the upstream and downstream side electrical resistive elements constant, or make currents flowing through these electrical resistive elements constant. Further, on the basis of the voltages applied in accordance with such constant temperature control or constant current control, a sensor output calculated value is calculated, and on the basis of the sensor output calculated value, and flow rate calibration curve data indicating the relationship between a sensor output calculated value and a flow rate, a flow rate corresponding to the sensor output calculated value is outputted.

Meanwhile, in the case where the type of gas to be used is not determined at the time of factory shipment, not the above-described corrosive or reactive gas, but inert gas (such as $N_2$) is flowed through a flow path, and on the basis of an actual flow rate of the inert gas and a corresponding sensor output calculated value, flow rate calibration curve data is calibrated. Accordingly, when the thermal flowmeter storing the flow rate calibration curve data calibrated using the inert gas measures the flow rate of corrosive gas or reactive gas without any correction, an actual flow rate is not correctly outputted. For this reason, when measuring the flow rate of gas of a type different from the gas used for the calibration, an outputted flow rate is corrected using a conversion factor that is a ratio between a flow rate of the gas used for the calibration and a flow rate of the gas currently flowing at each sensor output calculated value.

It is known that the conversion factor does not have a fixed value with respect to a flow rate, but as a flow rate increases, changes at an increase rate determined for each gas type. For example, in Patent Literature 1, a conversion factor is approximated as a cubic function of a flow rate, and the flow rate function representing the conversion factor is preliminarily stored for each gas type. Further, it is configured that on the basis of flow rate calibration curve data used for calibration and the flow rate function representing the conversion factor of that gas type, flow rate calibration curve data on the gas type is calculated, and an appropriate flow rate is outputted for any gas type.

However, in order to make it possible to calculate flow rate calibration curve data on each gas type in the configuration of a thermal flowmeter in Patent Literature 1, a flow rate function representing a conversion factor of that gas type should be identified in advance by experiment. Since a large number of gas types are present for use in a semiconductor manufacturing process, it takes time very much to identify flow rate functions representing conversion factors of all of possibly-used gas types.

Also, the conventional thermal flowmeter as described in Patent Literature 1 cannot automatically distinguish a gas type flowing through a flow path, and therefore every time a gas type to be flowed through the flow path is changed, a user is required to manually change settings such that a flow rate function representing a conversion factor of a corresponding gas type is used. In the semiconductor manufacturing process, in some cases, thermal flowmeters are respectively provided in multiple flow paths, and gas types flowing through the respective flow paths are different, so that it is very complicated for a user to make setting changes as described above to the respective thermal flow meters. For this reason, even in the case where the thermal flowmeter is configured to be able to correct the flow rate calibration data for each gas type, it is difficult to use the thermal flowmeter in an actual use environment.

CITATION LIST

Patent Literature

[Patent Literature 1]
Published Japanese Translation of PCT Application JP-A 2005-527819

SUMMARY OF INVENTION

Technical Problem

The present invention is made in consideration of the problems on a thermal flowmeter as described above, and intends to provide a thermal flowmeter that is adapted to be able to specify a fluid type flowing through a flow path, in particular, with use of only the configuration of the thermal flowmeter, or automatically calculate a parameter specific to a fluid type, such as a conversion factor or flow rate calibration curve data, and as a result, automatically change various types of settings appropriately for a fluid type to output a flow rate with high flow rate accuracy regardless of a gas type.

Also, the present invention intends to provide a fluid analysis device that on the basis of the relationship between a fluid type and a fluid-specific value calculated from voltages applied to respective electrical resistive elements, which has been first found by the present inventors in the process of examining the above problems, can specify not only a flow rate but a fluid type or a fluid physical property.

Solution to Problem

That is, the fluid analysis device of the present invention includes: a flow path through which measuring target fluid flows;
an upstream side electrical resistive element provided on an upstream side of the flow path; a downstream side electrical resistive element provided on a downstream side of the flow path; and a fluid-specific value calculation part that is configured to calculate a fluid-specific value on a basis of an upstream side parameter and a downstream side parameter, wherein the fluid specific value exhibits a specific value depending on thermal conductivity of the fluid; an upstream side parameter is a value related to a change rate of an upstream side voltage when a flow rate of the measuring target fluid changes, wherein the upstream side voltage is a voltage applied in order to make the upstream side electrical resistive element generate heat; a downstream side parameter is a value related to a change rate of a downstream side voltage when the flow rate of the measuring target fluid changes, wherein the downstream side voltage is a voltage applied in order to make the downstream side electrical resistive element generate heat.

Note that "an upstream side parameter that when a flow rate of the measuring target fluid changes, has a value related to a change rate of an upstream side voltage that is a voltage applied in order to make the upstream side electrical resistive element generate heat", or "a downstream side parameter that when the flow rate of the measuring target fluid changes, has a value related to a change rate of a downstream side voltage that is a voltage applied in order to make the downstream side electrical resistive element generate heat" refers to a parameter including at least a concept such as a slope that is a change rate of the upstream side voltage or the downstream side voltage with respect to the flow rate, a tangent corresponding to the slope, a change in the upstream side voltage or the downstream side voltage when changing the flow rate by some flow rate, or the difference between a voltage applied in a state where the fluid flows and a voltage applied in a state where the fluid does not flow. Also, "the type of fluid" refers to a concept that is not only in the case where the composition of a fluid molecule is of a single type but also as one type, distinguishes fluid in which multiple types of molecules are mixed.

Further, the above-described present invention is made on the basis of the fact that as a result of intensive examination, the present inventors have first found that the fluid-specific value that is a value calculated from an upstream side parameter and a downstream side parameter calculated from an upstream side voltage and a downstream side voltage applied in the fluid analysis device having the above-described configuration takes a specific value depending on the thermal conductivity of each fluid.

That is, by using the fluid-specific value calculated on the basis of the upstream side parameter and the downstream side parameter found by the present inventors, the thermal conductivity of the measuring target fluid flowing through the flow path can be specified from measured data.

Accordingly, for example, as long as the fluid analysis device is a thermal flowmeter adapted to measure the flow rate of the measuring target fluid, in the case of calculating the flow rate of the measuring target fluid on the basis of the upstream side voltage, the downstream side voltage, and the fluid-specific value, on the basis of the fluid-specific value, the thermal flow meter alone can automatically change flow rate calibration curve data depending on the thermal conductivity of the fluid or automatically switch to a conversion factor corresponding to the thermal conductivity of the fluid. From this, even in the case of application where the type of the measuring target fluid is appropriately changed, the thermal flowmeter of the present invention can automatically change settings for flow rate calculation to appropriate ones to constantly calculate a flow rate with high flow rate accuracy without troubling a user.

Further, the fluid-specific value corresponds to the thermal conductivity of the fluid on a one-to-one basis, and therefore it can be said that calculating the fluid-specific value is substantially equivalent to calculating the thermal conductivity of the fluid. Accordingly, by using the fact that a change rate of a conversion factor with respect to a flow rate depends on thermal resistivity that is the reciprocal of thermal conductivity, in the case where one conversion factor of fluid at some flow rate is known, a flow rate function representing conversion factors over the entire flow rate range can be estimated and calculated from a fluid-specific value. Accordingly, without identifying in advance and preparing pieces of flow rate calibration curve data or conversion factors for all possibly-used fluid types by actual measurement over the entire setting flow rate range as before, a flow rate can be calculated with high flow rate accuracy.

Also, in the case where the fluid analysis device is configured as a fluid property specification device adapted to specify a physical property, nature, or the like of the measuring target fluid, the type name of the fluid, a physical property such as the thermal conductivity can be specified on the basis of the fluid-specific value calculated in the fluid-specific value calculation part.

In order to make it possible to calculate an accurate flow rate regardless of a fluid type, it is only necessary that the thermal flowmeter is one including a flow rate calculation part that is configured to calculate the flow rate of the measuring target fluid on the basis of the upstream side voltage, the downstream side voltage, and the fluid-specific value calculated in the fluid-specific value calculation part.

In order to make it possible to express the relationship between the fluid-specific value and the thermal conductivity or thermal resistivity of the measuring target fluid as a simple linear expression, and accurately calculate appropriate flow rate calibration curve data or conversion factor for any measuring target fluid in accordance with a simple operation to increase flow rate accuracy, it is only necessary that the upstream side voltage is applied so as to make temperature of the upstream side electrical resistive element constant; the downstream side voltage is applied so as to make temperature of the downstream side electrical resistive element constant; and the fluid-specific value is a ratio between the upstream side parameter and the downstream side parameter.

In order to make it possible to, as long as flow rate calibration curve data is identified in advance with, for example, one type of inert gas as reference gas, without identifying flow rate calibration curve data on gas other than the inert gas, output a flow rate of fluid other than the inert gas with high flow rate accuracy, it is only necessary that the flow rate calculation part is configured to include: the fluid-specific value calculation part; a sensor output calculated value calculation part that is configured to calculate a sensor output calculated value on a basis of the upstream side voltage, the downstream side voltage, and a predetermined sensor output calculated value calculation expression; a flow rate calibration curve data storage part that is configured to store flow rate calibration curve data on one reference fluid, wherein the flow rate calibration curve data indicates a relationship between a sensor output calculated value and a flow rate; a CF calculation part that is configured to calculate a conversion factor of the measuring target fluid on a basis of the fluid-specific value; and a flow rate conversion part that is configured to convert the sensor output calculated value calculated in the sensor output calculated value calculation part into the flow rate of the measuring target fluid on a basis of the flow rate calibration curve data on the reference fluid and the conversion factor of the measuring target fluid.

In such a configuration, since the number of fluid types on which pieces of flow rate calibration curve data should be identified in advance is only one, an experiment for the identification does not require much time. Also, as long as a conversion factor at some flow rate of the measuring target fluid is known, a conversion factor at each flow rate range can be calculated from the fluid-specific value, and therefore even in the case where the type of the measuring target fluid is switched, the flow rate calibration curve data on the reference fluid can be automatically corrected with a conversion factor to constantly output a flow rate of a measuring target fluid with high flow rate accuracy.

In order to make it possible to accurately calculate a flow rate function representing the conversion factor of the measuring target fluid by utilizing the fact that a change ratio of the conversion factor to the flow rate depends on thermal resistivity that is the reciprocal of the thermal conductivity, it is only necessary that the CF calculation part is configured to calculate a CF change ratio on a basis of the fluid-specific value and to calculate the conversion factor at each flow rate of the measuring target fluid from a linear expression of the flow rate, wherein the CF change ratio is a change ratio of the conversion factor against the flow rate of the reference fluid; and the linear expression of the flow rate uses the CF change ratio as a slope.

For example, in order to make it possible to, while decreasing an operating load of a processor of the thermal flowmeter or the mass flow controller, in the case where a measuring target fluid type is changed, automatically use flow rate calibration curve data corresponding to a new measuring target fluid type to achieve high flow rate accuracy, it is only necessary that the flow rate calculation part includes: the fluid-specific value calculation part; a sensor output calculated value calculation part that is configured to calculate a sensor output calculated value on a basis of the upstream side voltage, the downstream side voltage, and a predetermined sensor output calculated value calculation expression; a flow rate calibration curve data storage part that is configured to store flow rate calibration curve data for each of thermal conductivities of multiple fluids, wherein the flow rate calibration curve data indicates a relationship between a sensor output calculated value and a flow rate; a flow rate calibration curve data acquisition part that is configured to acquire flow rate calibration curve data on the fluid of a type corresponding to the fluid-specific value calculated in the fluid-specific value calculation part from the flow rate calibration curve data storage part; and a flow rate conversion part that is configured to calculate the flow rate of the measuring target fluid on a basis of the flow rate calibration curve data acquired in the flow rate calibration curve data acquisition part, and the sensor output calculated value calculated in the sensor output calculated value calculation part.

In such a configuration, since only required is to operate only the fluid-specific value, appropriate flow rate calibration curve data can be used while decreasing the operating load.

In order to make it possible to, even in the case where the measuring target fluid is fluid configured to contain multiple types of molecules, grasp a mixing ratio among the respective molecules in the fluid, and grasp an appropriate conversion factor or flow rate calibration curve data as the entire fluid, and the concentrations of fluids containing the respective molecules, it is only necessary that the measuring target fluid is fluid in which a first fluid and a second fluid are mixed with a predetermined mixing ratio, and the thermal flowmeter further includes: a mixing ratio calibration curve data storage part that is configured to store mixing ratio calibration curve data indicating the relationship between a mixing ratio between the first fluid and the second fluid and a fluid-specific value of the measuring target fluid; and a mixing ratio calculation part that is configured to calculate the mixing ratio from the fluid-specific value of the measuring target fluid calculated in the fluid-specific value calculation part, and the mixing ratio calibration curve data.

In order to make it possible to, even in the case where the measuring target is fluid in which multiple types of molecules are mixed, calculate a conversion factor of the fluid in the mixed state from, for example, a known conversion factor of fluid configured to contain only each of the molecules, it is only necessary that the thermal flowmeter further includes a mixed fluid CF calculation part that on the basis of the mixing ratio calculated in the mixing ration calculation part, calculates a conversion factor of the measuring target fluid.

In the case of controlling the flow rate of the measuring target fluid, not only accurately grasping the flow rate but performing flow rate control using a control coefficient corresponding to the viscosity or the like of the measuring target fluid can further increase flow rate control accuracy. In order to enable such flow rate control, it is only necessary that a mass flow controller includes: a valve for controlling the flow rate of the measuring target fluid; and a valve control part that controls an opening level of the valve on the basis of a deviation between a measured flow rate value measured by the thermal flowmeter and a predetermined setting flow rate, and a control coefficient, in which the valve control part is configured to change the control coefficient, depending on the fluid-specific value calculated in the fluid-specific value calculation part. Such a configuration makes it possible to automatically switch to a control coefficient appropriate for a fluid type because a fluid-specific value corresponds to the thermal conductivity of fluid on a one-to-one basis.

In order to make it possible to analyze a physical property or the like of fluid itself by utilizing the finding by the present inventors that a fluid-specific value calculated from an upstream side parameter and a downstream side parameter has a predetermined relationship with the physical property or type of fluid, it is only necessary that the fluid analysis device is a fluid property specification adapted to specify the type or physical property of the measuring target fluid, and the fluid property specification device is configured as a specification part that specifies the type or physical property of the measuring target fluid on the basis of the fluid-specific value calculated in the fluid-specific value calculation part.

In order to make it possible to analyze fluid on the basis of upstream and downstream side voltages respectively applied to existing upstream and downstream side electrical resistive elements, it is only necessary to install, in an operating mechanism of an existing fluid analysis device, a program for a fluid analysis device, which is used for a fluid analysis device including: a flow path through which measuring target fluid flows; an upstream side electrical resistive element provided on an upstream side of the flow path; and a downstream side electrical resistive element provided on a downstream side of the flow path, and instructs a computer to fulfill a function as a fluid-specific value calculation part that is configured to calculate a fluid-specific value on a basis of an upstream side parameter and a downstream side parameter, wherein the fluid specific value exhibits a specific value depending on thermal conductivity of the fluid; an upstream side parameter is a value related to a change rate of an upstream side voltage when a flow rate of the measuring target fluid changes, wherein the upstream side voltage is a voltage applied in order to make the upstream side electrical resistive element generate heat; a downstream side parameter is a value related to a change rate of a downstream side voltage when the flow rate of the measuring target fluid changes, wherein the downstream side voltage is a voltage applied in order to make the downstream side electrical resistive element generate heat.

By using the above-described program for a fluid analysis device for an existing thermal flowmeter, a function that even in the case where the type of measuring target fluid is changed, can automatically switch to an appropriate conversion factor or flow rate calibration curve data to constantly output a flow rate with high accuracy can be added. Also, by using the above-described fluid analysis program for an existing fluid property specification device, a function for specifying the type of a measuring target or analyzing a physical property on the basis of the fluid-specific value can be added.

In addition, the program is not only distributed through the Internet or the like, but may be adapted to be recorded in a recording medium such as a CD-ROM, DVD, or flash memory and then installed using the recording medium.

Advantageous Effects of Invention

In the case where the fluid analysis device of the present invention is configured as, for example, the thermal flowmeter as described, on the basis of a fluid-specific value calculated from an upstream side parameter and a downstream side parameter, the type of measuring target fluid or a physical property such as thermal conductivity can be specified, and a conversion factor or fluid calibration curve data appropriate for the measuring target fluid can be automatically set. Accordingly, even in the case of application where the type of measuring target fluid is changed, a user can constantly measure a flow rate with high flow rate accuracy without performing any special operation.

Also, by utilizing the relationship between a fluid-specific value and the type or physical property of fluid, which has been first found by the present inventors, a fluid analysis device based on an unprecedented analysis principle can be provided.

REFERENCE SIGNS LIST

Figure 1:
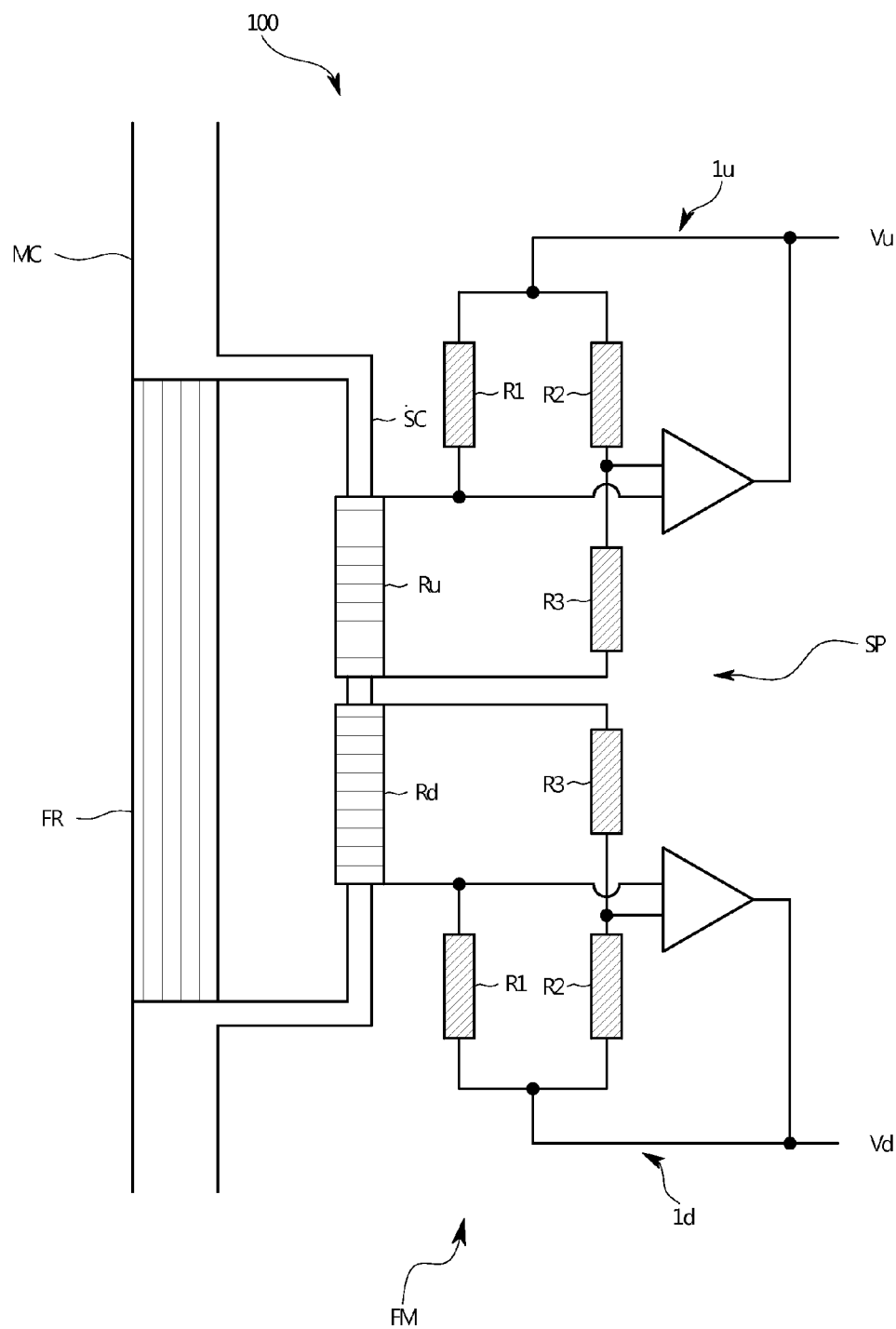
FIG. 1 is a schematic diagram illustrating a thermal flowmeter according to a first embodiment of the present invention.

100 Thermal flowmeter
101 Fluid analysis device
200 Mass flow controller
1$u$ Upstream side constant temperature control circuit
1$d$ Downstream side constant temperature control circuit
Ru Upstream side electrical resistive element
Rd Downstream side electrical resistive element
2 Flow rate calculation part
21 Sensor output calculated value calculation part
22 Fluid-specific value calculation part
23 CF calculation part
231 Mixed fluid CF calculation part
24 Flow rate calibration curve data storage part
25 Flow rate conversion part
27 Mixing ratio calculation part
28 Mixing ratio calibration curve data storage part
29 Flow rate calibration curve data acquisition part
3 Valve control part
4 Valve
5 Concentration monitoring part
6 Specification part
61 Thermal conductivity calculation part
62 Fluid type specification part
63 Corresponding data storage part

DESCRIPTION OF EMBODIMENTS

A first embodiment of the present invention will be described with reference to drawings. Note that a fluid analysis device in this description refers to one that analyzes a quantity related to a state such as a motion state of fluid, a quantity related to a physical property, or the like, and as a concept, includes at least a flowmeter adapted to measure a flow rate and a fluid property specification device adapted to specify the type or physical property of fluid. Also, the below-described fluid analysis part is configured as a flow rate calculation part when measuring a flow rate of fluid. On the other hand, when specifying the type or physical property of fluid, the fluid analysis part is configured as a specification part.

A thermal flowmeter 100 in the first embodiment is one that is used to, for example, in a non-contact manner, measure a flow rate of gas used for a semiconductor manufacturing process. Note that gases used for that purpose include various types of gases such as corrosive gases (such as $BCl_2$, $Cl_2$, $HCl$, and $ClF_3$) and reactive gases (such as $SiH_4$ and $B_2H_6$), and the thermal flowmeter 100 is calibrated on the basis of flow rates at the time when He as inert gas was flowed.

Also, the thermal flowmeter 100 is configured to automatically select a conversion factor CF appropriate for the type of gas flowing through a flow path, and regardless of the type of gas, constantly output an accurate flow rate. Note that the type of gas flowing through the flow path is switched depending on the intended use; however, the first embodiment is adapted to flow a single type of gas.

More specifically, the thermal flowmeter 100 is one that as illustrated in a schematic diagram of FIG. 1, includes: a main flow path MC through which gas as fluid flows; a sensor flow path SC that is a narrow tube branching from the main flow path MC, through which the gas branched from the main flow path MC flows; a flow rate measuring mechanism FM for measuring a flow rate on the basis of the gas flowing through the sensor flow path SC; and a laminar flow element FR that is provided between a branching point and a meeting point of the branching flow path in the main flow path MC and as a fluid resistor having multiple internal flow paths. In addition, the laminar flow element FR is configured such that a flow dividing ratio between the main flow path MC and the sensor flow path SC has a predetermined design value, and as the laminar flow element FR, for example, one formed by inserting multiple narrow tubes into an outer tube, or one formed by stacking multiple thin flat plates having many through-holes can be used.

The sensor flow path SC is formed of a substantially U-shaped hollow narrow tube, and the narrow tube is made of metal such as stainless steel. On a linear part corresponding to the bottom part of the U-shaped narrow tube, two electrical resistive elements of the flow rate measuring mechanism FM are wound.

The flow rate measuring mechanism FM is configured to include: a sensor part SP that gives an output corresponding to the flow rate of the gas flowing through the sensor flow path SC; and a flow rate calculation part 2 that on the basis of the output from the sensor part SP, calculates a mass flow rate of the gas flowing through the main flow path MC.

The sensor part SP includes: an upstream side electrical resistive element Ru that is a coil wound on the outer surface of the narrow tube on the upstream side of the sensor flow path SC; and a downstream side electrical resistive element Rd that is a coil wound on the outer surface of the narrow tube on the downstream side of the sensor flow path SC. Each of the upstream side electrical resistive element Ru and the downstream side electrical resistive element Rd is formed of a heat generating resistance wire of which an electrical resistance value increases/decreases as temperature changes, and adapted to be able to serve as both heating means and temperature detecting means as one member.

Further, the sensor part SP is of a constant temperature type, in which a bridge circuit including the upstream side electrical resistive element Ru as a part constitutes an upstream side constant temperature control circuit 1u and a bridge circuit including the downstream side electrical resistive element Rd as a part constitutes a downstream side constant temperature control circuit 1d.

The upstream side constant temperature control circuit 1u includes: the upstream side bridge circuit formed by parallel connecting a series resistor group including the upstream side electrical resistive element Ru and a temperature setting resistor R1 connected in series with the upstream side electrical resistive element Ru, and a series resistor group including two fixed resistors R2 and R3 connected in series; and a feedback control circuit including an operational amplifier that feeds the difference (Vu) in potential between the connecting point between the upstream side electrical resistive element Ru and the temperature setting resistor R1 and the connecting point between the two fixed resistors back to the upstream side bridge circuit to balance the upstream side bridge circuit.

As with the upstream side constant temperature control circuit 1u, the downstream side constant temperature control circuit 1d also includes: the downstream side bridge circuit formed by parallel connecting a series resistor group including the downstream side electrical resistive element Rd and a temperature setting resistor R1 connected in series with the downstream side electrical resistive element Rd, and a series resistor group including two fixed resistors R2 and R3 connected in series; and a feedback control circuit including an operational amplifier that feeds the difference (Vd) in potential between the connecting point between the downstream side electrical resistive element Rd and the temperature setting resistor R1 and the connecting point between the two fixed resistors back to the downstream side bridge circuit to balance the downstream side bridge circuit.

Note that the upstream side electrical resistive element Ru and the downstream side electrical resistive element Rd are heat sensitive resistive bodies, and configured using materials having the same temperature coefficient of resistance. In addition, the upstream side electrical resistive element Ru and the downstream side electrical resistive element Rd are feedback-controlled so as to have the same resistance values as those of the temperature setting resistors R1 by the respective feedback control circuits. That is, since the resistance values are kept at a constant, the voltages Vu and Vd are controlled such that the temperatures of the upstream side electrical resistive element Ru and the downstream side electrical resistive element Rd are also kept constant. In the first embodiment, Vu and Vd are respectively used as the upstream side voltage Vu and the downstream side voltage Vd that are voltages applied in order to make the upstream side electrical resistive element Ru and the downstream side electrical resistive element Rd generate heat.

The flow rate calculation part 2 (fluid analysis part) is one that is configured to calculate the flow rate of the measuring target gas flowing through the sensor flow path SC on the basis of the upstream side voltage Vu that is the voltage applied in order to make the upstream side electrical resistive element Ru generate heat and the downstream side voltage Vd that is the voltage applied in order to make the downstream side electrical resistive element Rd generate heat. In addition, a so-called computer including a memory, a CPU, input/output means, an A/D converter, a D/A converter, and the like executes a flow rate calculation program stored in the memory, and thereby the flow rate calculation part 2 realizes its functions. That is, as illustrated in a functional block diagram of FIG. 2, the flow rate calculation part 2 is configured to realize functions as at least a sensor output calculated value calculation part 21, a fluid-specific value calculation part 22, a CF calculation part 23, a flow rate calibration curve data storage part 24, and a flow rate conversion part 25.

The respective parts will be described.

The sensor output calculated value calculation part 21 is one that is configured to calculate a sensor output calculated value on the basis of the upstream side voltage Vu, the downstream side voltage Vd, and a predetermined sensor output calculated value calculation expression. In the first embodiment, a value obtained by dividing the difference between the upstream side voltage Vu and the downstream side voltage Vd by the sum of the upstream side voltage Vu and the downstream side voltage Vd is defined as the sensor output calculated value, and the sensor output calculated value calculation expression is expressed as follows using the sensor output calculated value Vc, the upstream side voltage Vu, and the downstream side voltage Vd.

$$Vc=(Vu-Vd)/(Vu+Vd)$$

Here, (Vu−Vd) is a function depending on the flow rate and temperature of the fluid, and (Vu+Vd) is a function depending on only the temperature of the fluid. Accordingly, the sensor output calculated value Vc is a function that eliminates the effect of the temperature of the fluid and depends on only the flow rate of the fluid.

The fluid-specific value calculation part 22 is one that is configured to calculate a fluid-specific value N on the basis of an upstream side parameter ΔVu that has a value related to a change rate of the upstream side voltage Vu when the flow rate of the measuring target gas changes, and a downstream side parameter ΔVd that has a value related to a change rate of the downstream side voltage Vd when the flow rate of the measuring target gas changes. The relationship among the upstream side voltage Vu, upstream side parameter ΔVu, downstream side voltage Vd, and downstream side parameter ΔVd will now be described.

Figure 3:
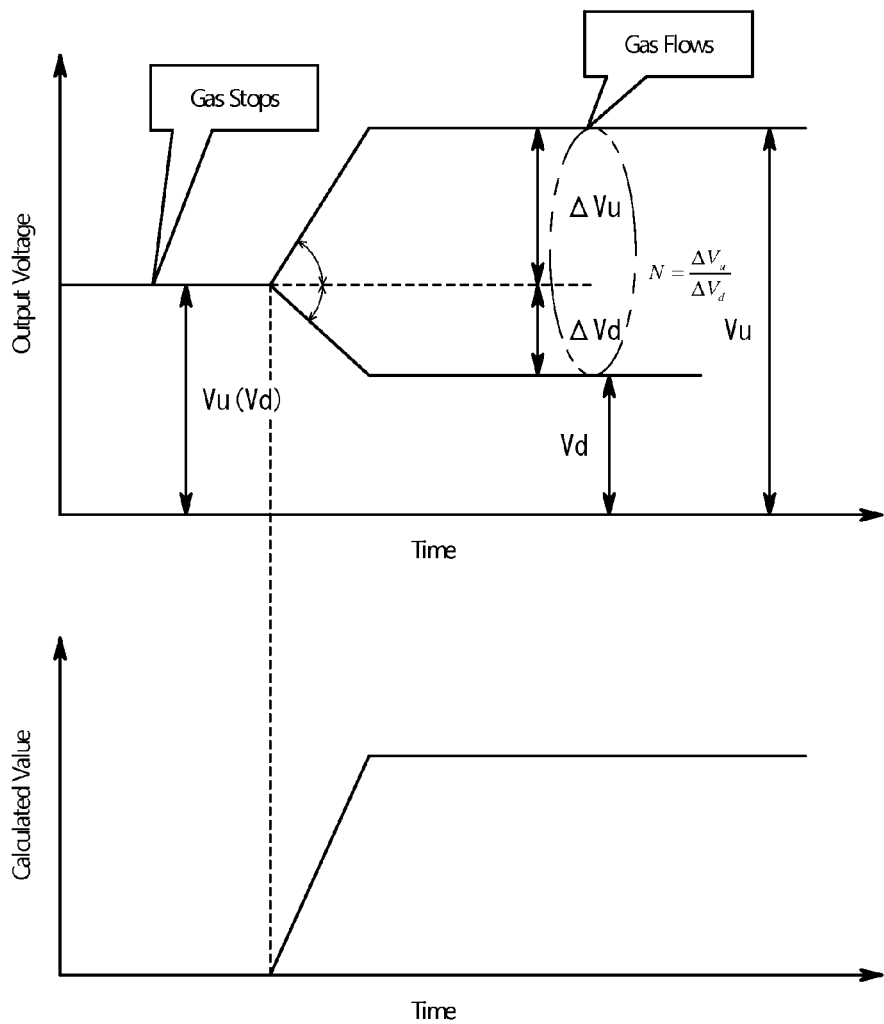
FIG. 3 is a schematic graph illustrating the definitions of an upstream side parameter and a downstream side parameter in the first embodiment.

FIG. 3 is a graph illustrating the relationships between the flow rate, and the upstream side voltage Vu and the downstream side voltage Vd. In the case of the thermal flowmeter 100 of the constant temperature type, when the gas does not flow through the sensor flow path SC, the upstream side voltage Vu and the downstream side voltage Vd have substantially the same voltage value. This is because since the gas does not flow, heat applied by the upstream side electrical resistive element Ru never moves to the downstream side electrical resistive element Rd on the downstream side, and therefore the upstream side electrical resistive element Ru and the downstream side electrical resistive element Rd should be applied with the same voltage in order to keep a predetermined temperature.

On the other hand, when the gas flows, heat applied to the gas by the upstream side electrical resistive element Ru moves to the downstream side electrical resistive element Rd. As a result, in order to attempt to keep the same temperature, the upstream side electrical resistive element Ru that is on a side from which heat is taken requires a larger voltage, whereas for the downstream side electrical resistive element Rd that is on a side to which the heat is given from the upstream side, a small voltage as compared with when the gas does not flow is sufficient. For this reason, in proportion to the flow rate of the gas flowing through the sensor flow path SC, the upstream side voltage Vu increases, and the downstream side voltage Vd decreases. In addition, the change rates of the upstream side voltage Vu and the downstream side voltage Vd with respect to the flow rate change depending on the type of the gas, more specifically depending on the thermal conductivity of the gas. The upstream side parameter ΔVu and the downstream side parameter ΔVd represent the change rates of the upstream side voltage Vu and the downstream side voltage Vd with respect to the flow rate, and in the first embodiment, as illustrated in the graph of FIG. 3, values obtained by subtracting the upstream side voltage Vu and the downstream side voltage at the time when the gas does not flow or stops from the upstream side voltage Vu and the downstream side voltage Vd at the time when the gas flows at some flow rate are respectively defined as the upstream side parameter ΔVu and the downstream side parameter ΔVd. In addition, as the upstream side parameter ΔVu and the downstream side parameter ΔVd, various parameters such as the slopes of linear functions representing the upstream side voltage Vu and the downstream side voltage Vd using the flow rate as variables, or tangents corresponding to the slopes may be used.

Further, in the first embodiment, the fluid-specific value calculation part 22 is configured to calculate a ratio between the upstream side parameter ΔVu and the downstream side parameter ΔVd as the fluid-specific value N. More specifically, the fluid-specific value N is made equal to a value obtained by dividing the upstream side parameter ΔVu by the downstream side parameter ΔVd. Between the fluid-specific value N and thermal resistivity that is the reciprocal of thermal conductivity specific to each gas type, there is a correlation, which can be described as a linear expression. In other words, the fluid-specific value N is a value specific to that gas type, and by substituting the fluid-specific value N into a predetermined calculation expression, the thermal resistivity or the thermal conductivity can be calculated. Accordingly, by calculating the fluid-specific value N, the type of gas currently flowing through the sensor flow path SC can be specified, and the thermal resistivity or thermal conductivity of flowing fluid can be calculated, and used for correction when calculating a flow rate. The relationship between the fluid-specific value N of each gas type calculated on the basis of the upstream side parameter ΔVu and the downstream side parameter ΔVd and thermal resistivity or thermal conductivity is one that has been first found by the present inventors as a result of intensive examination.

Next, the reason why the fluid-specific value N calculated from the upstream side parameter ΔVu and the downstream side parameter ΔVd is a value specific to each gas type, and has the predetermined relationship with thermal resistivity or thermal conductivity will be quantitatively described.

Figure 4:
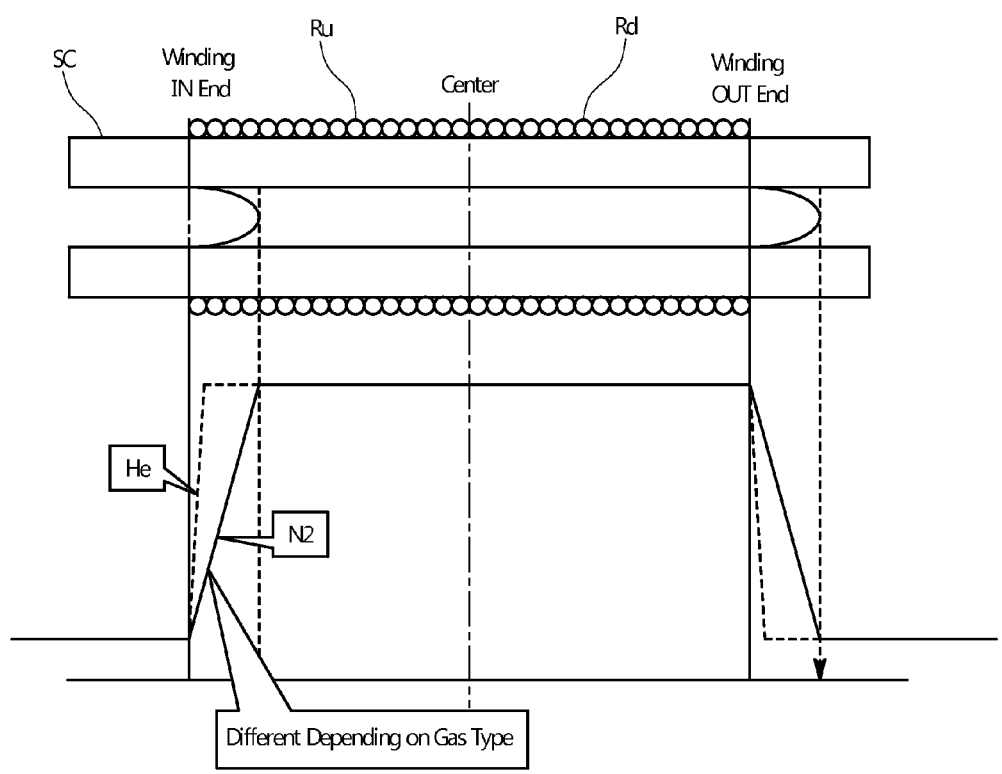
FIG. 4 is a schematic diagram illustrating a main cause why a fluid-specific value is different depending on the thermal conductivity of each fluid.

As illustrated in a graph of FIG. 4, in the case where the type of gas flowing through the sensor flow path SC, i.e., the thermal conductivity of the gas is different, a temperature distribution in a part of the sensor flow path SC where the upstream side electrical resistive element Ru or the downstream side electrical resistive element Rd is wound is also different. More specifically, in the case where thermal conductivity is high like He gas, and heat is quickly transferred, within a range where the upstream side electrical resistive element Ru and the downstream side electrical resistive element Rd are wound, a temperature rise occurs without any substantial delay. In the case of gas having high thermal conductivity like He gas, since heat is transferred between the upstream side and the downstream side on a substantially one-to-one basis, the absolute values of the upstream side parameter ΔVu and the downstream side parameter ΔVd are substantially the same values, and the fluid-specific value N is a value close to 1. On the other hand, in the case of $N_2$ gas having low thermal conductivity as compared with He gas, the temperature distribution where at a point on a slightly inner side of an inlet on the upstream side electrical resistive element Ru side, a setting temperature is reached, whereas at a point on a slightly outer side of an outlet on the downstream side electrical resistive element Rd side, an original temperature is restored is obtained. That is, since heat given to the $N_2$ gas on the upstream side is transferred to the downstream side with a slight delay, the absolute value of the downstream side parameter ΔVd is small as compared with the absolute value of the upstream side parameter ΔVu, and the fluid-specific value N is a value smaller than 1.

Next, the CF calculation part 23 illustrated in FIG. 2 will be described.

Figure 5A:
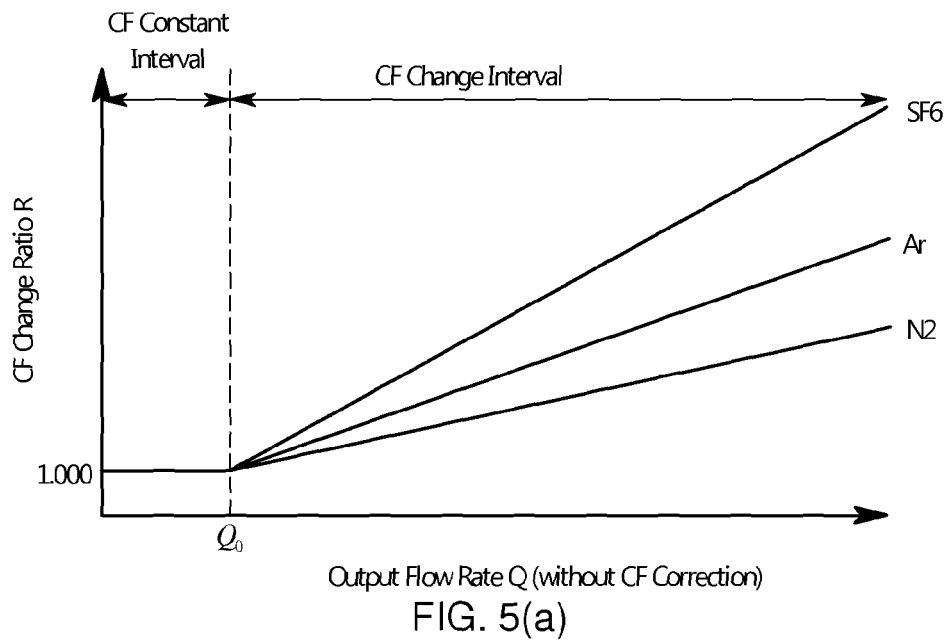
FIGS. 5(a) and 5(b) are schematic graphs illustrating the tendency of an error in conversion factor with respect to a flow rate, and the relationship between the fluid-specific value and a CF change ratio.
Figure 5B:
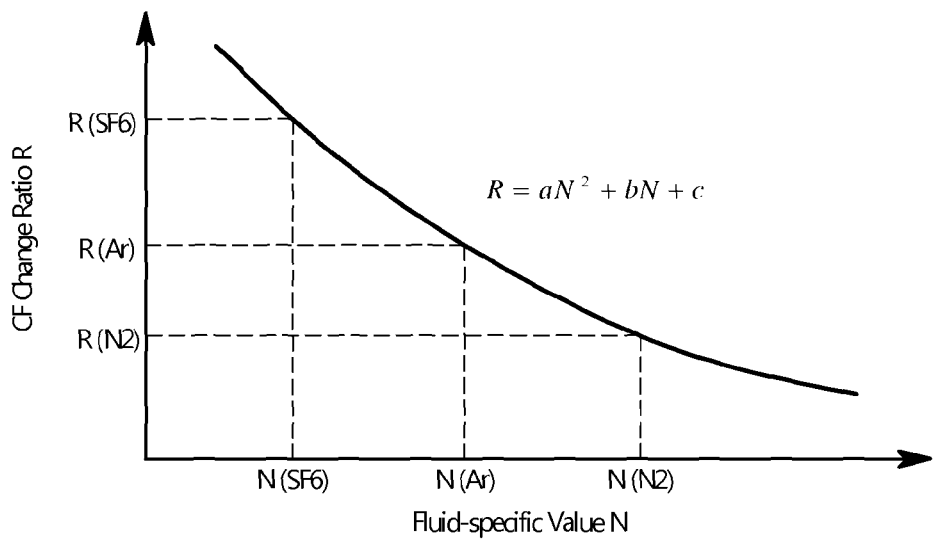

The CF calculation part 23 is one that on the basis of the fluid-specific value N, calculates the conversion factor CF of the gas flowing through the sensor flow path SC as the measuring target fluid. Note that the conversion factor CF refers to a factor used to correct a flow rate value outputted when a gas type different from the gas type used to calibrate the thermal flowmeter 100 flows. In the first embodiment, since the flow rate calibration curve data Eq indicating the relationship between a sensor output calculated value Vc and a flow rate of an actually flowing gas is calibrated with He gas, in the case where gas flowing through the flow path is He gas, the conversion factor CF is 1, whereas in the case of another gas type, a specific conversion factor CF is calculated. Meanwhile, the conversion factor CF does not take a constant value at all flow rate values, but takes a value changing with increasing a flow rate. For this reason, the CF calculation part 23 is configured to, on the basis of the fluid-specific value N, calculate a CF change ratio R that is a change ratio of the conversion factor CF to a flow rate calculated on the basis of the gas used for the calibration, and from a linear expression of a flow rate, which includes the CF change ratio R as a slope, calculate the conversion factor CF at each flow rate of the measuring target gas. More specifically, as illustrated in a graph of FIG. 5(a), as the flow rate increases, an error of the conversion factor CF tends to increase. Also, in the interval where the flow rate is from zero to a predetermined flow rate Q0 (a fixed interval), the conversion factor CF takes a constant value regardless of a gas type, but when the flow rate exceeds the predetermined flow rate Q0 (a CF change interval), as the flow rates increases, the conversion factor CF increases at a slope specific to each gas type. The CF change ratio R that is a slope specific to that gas type in the CF change interval depends on thermal resistivity, and therefore also depends on the fluid-specific value N having a one-to-one correspondence relationship with the thermal resistivity. Accordingly, the CF change ratio R can be expressed as a quadratic function of the fluid-specific value N.

For this reason, the CF calculation part 23 is configured to first calculate the CF change ratio R from the fluid-specific value N calculated in the fluid-specific value calculation part 22, and uses the calculated CF change ratio R and $CF_0$ that is a conversion factor CF at the predetermined flow rate Q0 to calculate the conversion factor CF in the CF change interval as a linear expression of the flow rate. Given that an output flow rate based on the reference gas is Q, a specific expression is as follows.

$$CF=CF_0(1+(R-1)*Q/100)$$

Figure 2:
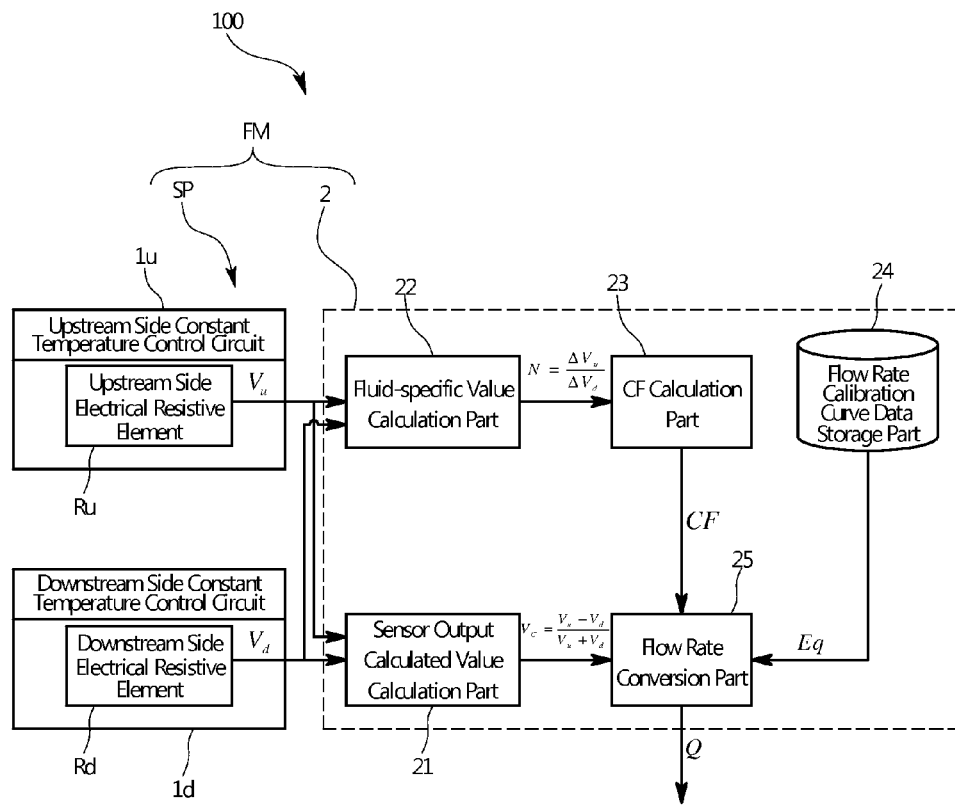
FIG. 2 is a functional block diagram illustrating a functional configuration of the thermal flowmeter in the first embodiment.

The flow rate calibration curve data storage part 24 illustrated in FIG. 2 is one that is configured to store the flow rate calibration curve data Eq indicating the relationship between a sensor output calculated value and a flow rate of He gas as one reference gas. More specifically, the flow rate calibration curve data storage par 24 stores the relationship between the flow rate of He gas and the sensor output calculated value Vc as a linear expression. That is, in the case where gas flowing through the sensor flow path SC is He, by substituting the sensor output calculated value Vc into the flow rate calibration curve data Eq, a flow rate of currently flowing He is obtained.

The flow rate conversion part 25 is one that on the basis of the flow rate calibration curve data Eq on the reference fluid and the conversion factor CF of the measuring target gas, is configured to convert the sensor output calculated value calculated in the sensor output calculated value calculation part 21 into the flow rate of the measuring target gas. That is, the flow rate conversion part 25 is one that multiplies a flow rate of the reference gas, which is calculated by substituting the sensor output calculated value Vc into the flow rate calibration curve data Eq, by the conversion factor CF, and thereby outputs a flow rate corresponding to the gas type currently flowing through the sensor flow path SC.

As described, the thermal flowmeter 100 in the first embodiment is configured to calculate a fluid-specific value N corresponding on a one-to-one basis to thermal resistivity or thermal conductivity that is specific to each gas type and calculated on the basis of the upstream side parameter ΔVu and the downstream side parameter ΔVd. Also, on the basis of the fluid-specific value N, the thermal flowmeter 100 can appropriately automatically calculate a conversion factor CF necessary to correct a flow rate value. Accordingly, even when a gas type is switched, a user is not required to set a conversion factor CF to be used, and on the basis of a conversion factor CF calculated from a fluid-specific value N, a flow rate can be constantly accurately outputted regardless of a gas type.

When thinking from another aspect, the thermal flowmeter 100 in the first embodiment can obtain a physical property of each gas type, such as thermal resistivity or thermal conductivity, and eventually a conversion factor CF on the basis of an upstream side voltage Vu and a downstream side voltage Vd that have values indispensable for calculating a flow rate and are applied in order to make the upstream side electrical resistive element Ru and the downstream side electrical resistive element Rd generate heat, respectively, without separately adding a sensor. That is, without changing a hardware configuration of a conventional thermal flowmeter 100, a physical property of measuring target gas, which has not been obtainable, such as a conversion factor CF, can be obtained on the basis of a fluid-specific value N only by changing software, and therefore the accuracy of a flow rate output can be improved.

The reason why the need to separately provide a sensor for specifying a gas type, or the need for a user to change settings of a thermal flowmeter 100 can be eliminated is based on the fact that as a result of intensive examination, the present inventors have first found that a fluid-specific value N calculable from voltages obtained in the thermal flowmeter 100 and thermal resistivity or thermal conductivity specific to each gas type have a one-to-one relationship.

Next, a thermal flowmeter 100 in a second embodiment, and a mass flow controller 200 using the thermal flowmeter 100 will be described. Note that members corresponding to those in the first embodiment are denoted by the same reference signs. Also, in the second embodiment, gas flowing through a flow path is not limited to a single type of gas, and mixed gas in which two types of gases are mixed may flow through the flow path.

Figure 6A:
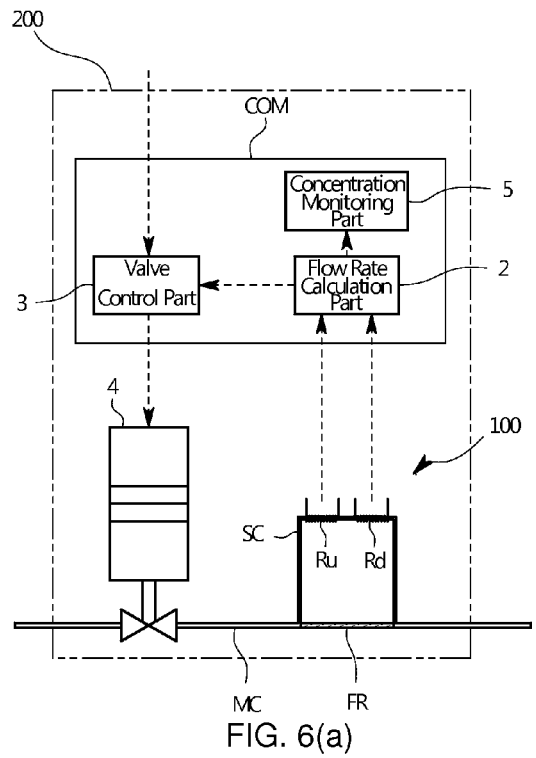
FIGS. 6(a) and 6(b) are schematic diagrams illustrating a thermal flowmeter and a mass flow controller according to a second embodiment of the present invention.
Figure 6B:
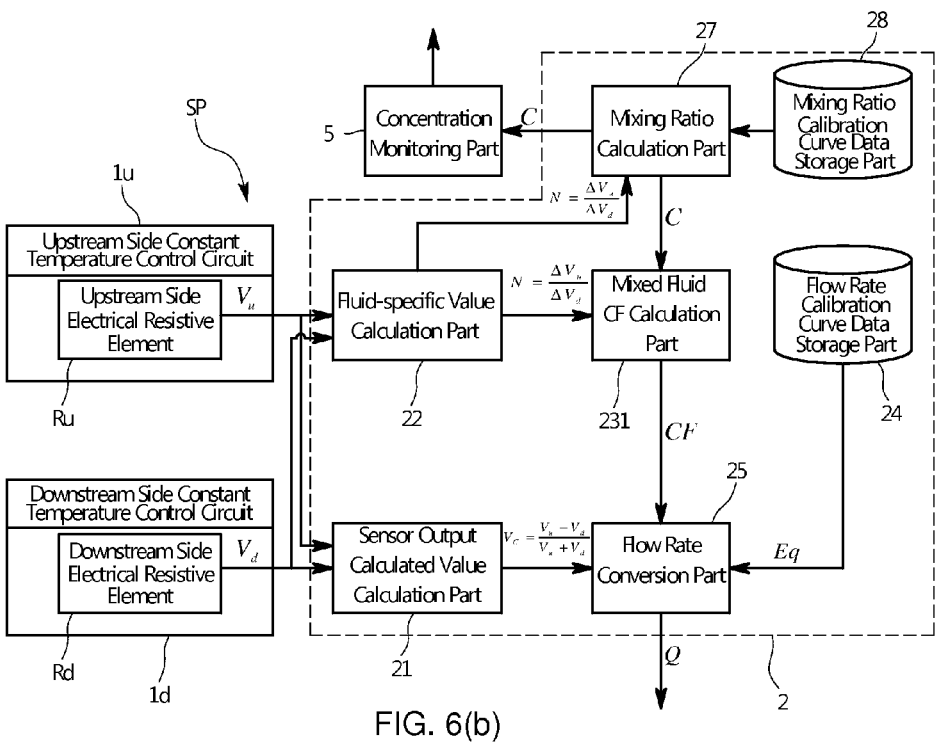

As illustrated in FIG. 6(a), the mass flow controller 200 is one that includes: a valve 4 provided in a main flow path MC; the thermal flowmeter 100 provided on the downstream side of the valve 4; and an operating mechanism COM that controls various types of operations such as a flow rate operation in the thermal flowmeter 100 and a control operation for controlling an opening level of the valve 4. The valve 4 is, for example, a piezo valve 4, and the opening level thereof can be controlled by an applied voltage from fully closing to fully opening. The operating mechanism COM is one of which functions are realized by a so-called computer including a CPU, a memory, input/output means, an A/D converter, a D/A converter, and the like, and as illustrated in FIG. 6(b), configured to fulfill functions as a flow rate calculation part 2 as part of the thermal flow rate sensor, a concentration monitoring part 5 adapted to monitor the concentration of a specific type of gas in the gas flowing through the flow path, and a valve control part 3 adapted to control the opening level of the valve 4 on the basis of an output flow rate outputted from the thermal flowmeter 100 in such a way that a program stored in the memory is executed.

The respective parts will be described.

The flow rate calculation part 2 also has a configuration common to that in the first embodiment, but is different in that the flow rate calculation part 2 can also cope even in the case where fluid flowing through the flow path is mixed gas in which multiple types of gases are mixed. More specifically, the flow rate calculation part 2 in the second embodiment has a sensor output calculated value calculation part 21, fluid-specific value calculation part 22, flow rate calibration curve data storage part 24, and flow rate conversion part 25 as substantially the same configuration as that in the first embodiment. On the other hand, the flow rate calculation part 2 in the second embodiment is different in having a mixing ratio calculation part 27, mixing ratio calibration curve data storage part 28, and mixed fluid CF calculation part 231 in place of the CF calculation part 23 in the first embodiment.

In the following description, matters described in the first embodiment will be omitted, and a configuration specific to the second embodiment will be described in detail. In addition, in the second embodiment, measuring target fluid is one in which two types of gases are mixed with a predetermined mixing ratio, and the case where a first fluid is $H_2$ gas, and a second fluid is $CO_2$ gas will be described. Also, the mixing ratio and concentration will be described with a focus on the $H_2$ gas.

The mixing ratio calibration curve data storage part 28 is one that is configured to store mixing ratio calibration curve data indicating the relationship between a fluid-specific value N of mixed gas in a state where the $H_2$ gas and the $CO_2$ gas are mixed with each of various mixing ratios and that mixing ratio between the $H_2$ gas and the $CO_2$ gas. That is, in the case where multiple types of gases are mixed, a fluid-specific value N of the mixed gas has a value obtained by calculating a weighted average of fluid-specific values N of the respective gases on the basis of a mixing ratio (concentration). More specifically, given that the concentration of a first fluid is C1, the concentration of a second fluid is C2, a fluid-specific value N of the first fluid is N1, and a fluid-specific value of the second fluid is N2, a fluid-specific value $N_{mix}$ of mixed fluid can be expressed as follows.

$$N_{mix}=N1 \cdot C1/(C1+C2)+N2 \cdot C2/(C1+C2)$$

Figure 7A:
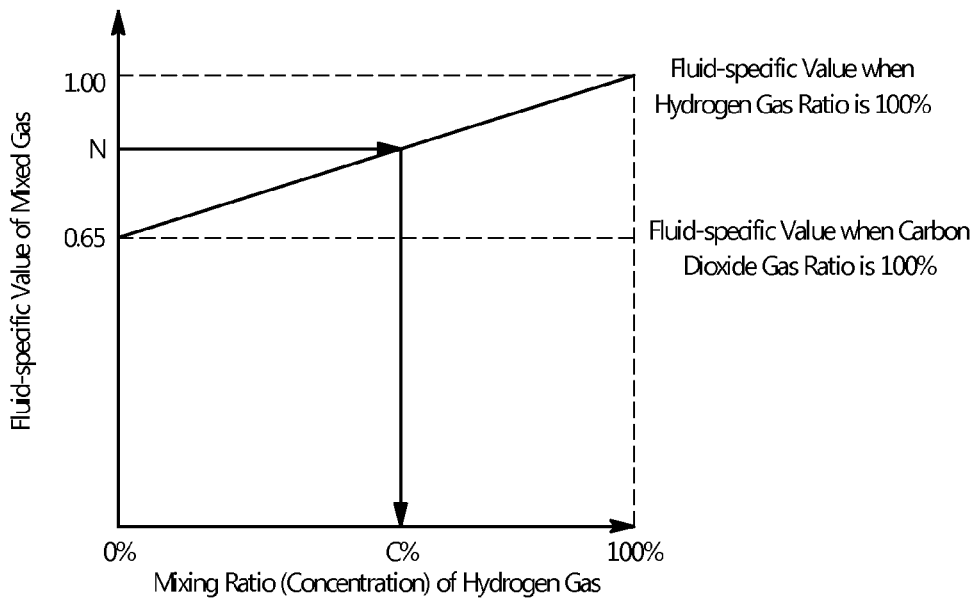
FIGS. 7(a) and 7(b) are schematic diagrams illustrating the relationship between a fluid-specific value and a mixing ratio, and the relationship between the mixing ratio and a conversion factor of mixed gas.

The mixing ratio calibration curve data storage part 28 stores the mixing ratio calibration data indicating the relationship between a mixing ratio of the $H_2$ gas and a corresponding fluid-specific value N of the mixed gas as illustrated in FIG. 7(a) as a linear expression on the basis of the above expression.

The mixing ratio calculation part 27 is one that is configured to calculate a mixing ratio from a fluid-specific value N of the measuring target fluid calculated in the flow rate calculation part 2 and the mixing ratio calibration curve data. More specifically, the mixing ratio calculation part 27 calculates a current mixing ratio of the $H_2$ gas flowing through the sensor flow path SC from a fluid-specific value N calculated by the fluid-specific value calculation part 22 on the basis of an upstream side parameter ΔVu and a downstream side parameter ΔVd while referring to the mixing ratio calibration curve data in FIG. 7(a). The mixing ratio calculation part 27 is configured to, when the fluid-specific value N calculated from the fluid-specific value calculation part 22 is changed, recalculate the mixing ratio.

Figure 7B:
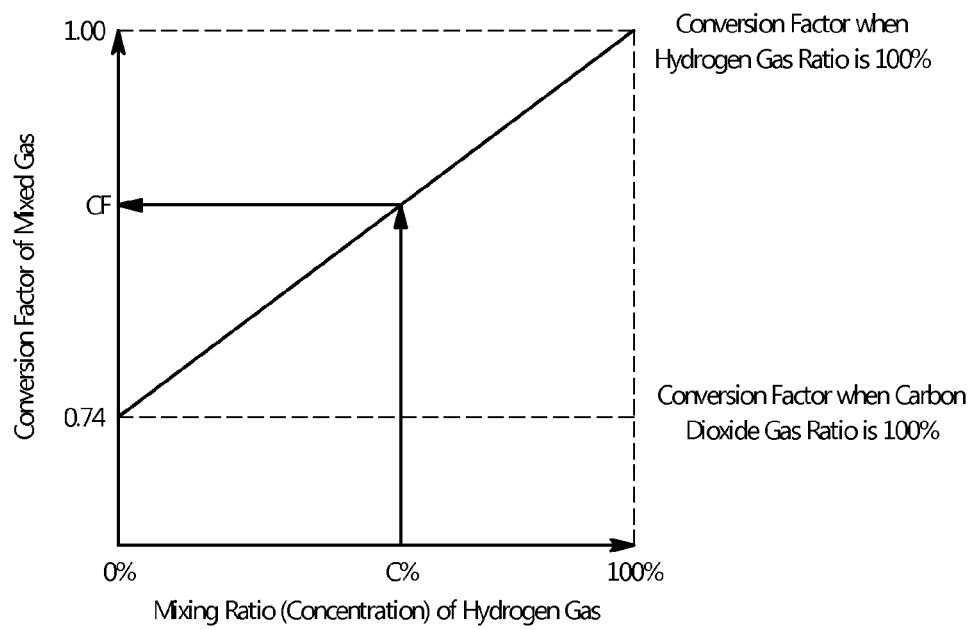

The mixed fluid CF calculation part 231 is one that is configured to calculate a conversion factor CF of the measuring target fluid on the basis of the mixing ratio calculated in the mixing ratio calculation part 27. More specifically, the mixed fluid CF calculation part 231 is configured to calculate the conversion factor CF of the mixed gas by calculating a weighted average of a conversion factor CF of the $H_2$ gas and a conversion factor CF of the $CO_2$ gas on the basis of the calculated mixing ratio. That is, while referring to conversion factor CF calibration curve data indicating the relationship between a mixing ratio of the $H_2$ gas and a conversion factor CF of the mixed gas as illustrated in FIG. 7(b), a corresponding conversion factor CF is obtained from the calculated mixing ratio. In addition, the mixed fluid CF calculation part 231 is also configured to, when the mixing ratio calculated by the mixing ratio calculation part 27 is changed, recalculate the conversion factor CF. Accordingly, when the composition of the mixed gas is changed to change the fluid-specific value N, the mixing ration calculation part 27 and the mixed fluid CF calculation part 231 calculate the conversion factor CF correspondingly to the change, and therefore an outputted flow rate can be made constantly accurate without giving rise to any flow rate error.

The concentration monitoring part 5 is one that monitors the concentration of the $H_2$ gas on the basis of the mixing ratio obtained in the mixing ratio calculation part 27. That is, the concentration monitoring part 5 monitors the concentration of $H_2$ in the mixed gas flowing through the sensor flow path SC on the basis of the fluid-specific value N, which is constantly outputted and calculated from the upstream side parameter ΔVu and the downstream side parameter ΔVd, without separately providing a concentration sensor in the sensor flow path SC. The concentration of the $H_2$ gas outputted from the concentration monitoring part 5 is used to, for example control the mass flow controller 200 or display a current state of the mixed gas externally.

The valve control part 3 is one that feedback-controls the opening level of the valve 4 so as to decrease the deviation between an output flow rate value outputted from the flow rate conversion part 25 of the thermal flowmeter 100 and a setting flow rate value preset by a user. For example, the valve control part 3 is one that controls the opening level of the valve 4 on the basis of PID control, and configured to change PID coefficients used for the PID control on the basis of the fluid-specific value N calculated in the fluid-specific calculation part 22 or the concentration of the $H_2$ gas outputted from the concentration monitoring part 5. More specifically, since from a value of the fluid-specific value N, the type of gas flowing through the sensor flow path SC is known, and the concentrations of respective gases are known from the concentration monitoring part 5, a parameter of the gas flowing through the flow path, such as viscosity, can also be estimated. Accordingly, the valve control part 3 is adapted to set the PID coefficients that make response characteristics best depending on a gas type specified from the fluid-specific value N, the viscosity of it, or the like. As the PID coefficients to be set depending on the fluid-specific value N, optimum ones may be predetermined by, for example, experiment or the like.

As described, even in the case of mixed gas in which multiple types of gases are mixed, the thermal flowmeter 100 and the mass flow controller 200 in the second embodiment can calculate a conversion factor CF of the mixed gas on the basis of a fluid-specific value N of the mixed gas, and correct a flow rate error. Also, even in the case of mixed gas of which a mixing ratio changes, a conversion factor CF appropriate for the composition of the mixed gas can be successively calculated to correct a flow rate error, and therefore an accurate flow rate can be constantly outputted.

Further, since an accurate flow rate is constantly outputted regardless of the type or composition of flowing gas by the thermal flowmeter 100, a flow rate of gas actually flowing can be accurately kept at a setting flow rate value, and therefore flow rate control accuracy can be increased.

Still further, since the concentration of the $H_2$ gas in the mixed gas can be monitored in the concentration monitoring part 5, while performing flow rate control, concentration control can also be performed together. The concentration measurement of the $H_2$ gas does not require the direct contact of a platinum sensor or the like with the fluid, which has been required in the past, but can be performed in a non-contact manner. As a result, even in the case where mixed gas contains reactive gas or corrosive gas, concentration can be easily measured.

Figure 8:
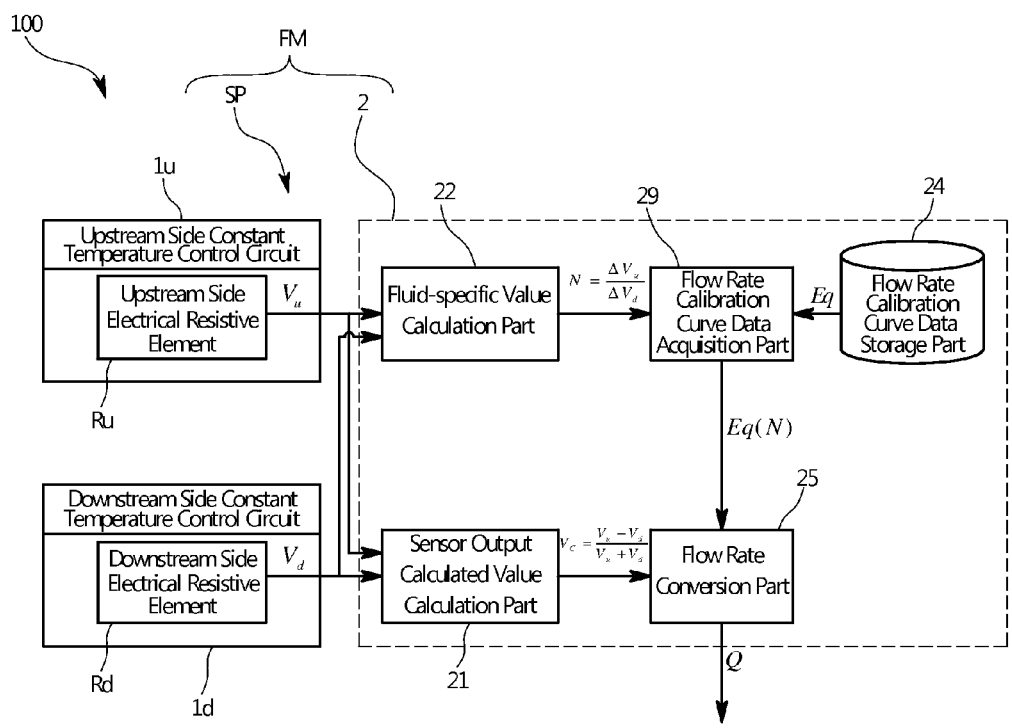
FIG. 8 is a functional block diagram illustrating a thermal flowmeter according to a third embodiment of the present invention.

Next, a thermal flowmeter 100 in a third embodiment will be described with reference to FIG. 8. In the description of the third embodiment as well, members corresponding to those in the first embodiment are denoted by the same reference signs.

The thermal flowmeter 100 in the third embodiment is configured not to calculate a conversion factor CF, but to prepare calibrated flow rate calibration curve data Eq for each fluid type in advance, then acquire flow rate calibration curve data Eq corresponding to fluid estimated to currently flow through a flow path, and calculate a flow rate.

That is, a flow rate calculation part 2 in the third embodiment includes a sensor output calculated value calculation part 21, fluid-specific value calculation part 22, flow rate calibration curve data storage part 24, flow rate calibration curve data acquisition part 29, and flow rate conversion part 25, and as compared with the flow rate calculation part 2 in the first embodiment, the sensor output calculated value calculation part 21, fluid-specific value calculation part 22, and flow rate conversion part 25 have substantially the same configurations, respectively. On the other hand, it is not that the flow rate calibration curve data storage part 24 in the third embodiment stores only flow rate calibration curve data Eq on reference fluid as in the first embodiment, but the flow rate calibration curve data storage part 24 stores flow rate calibration curve data Eq on each of possibly-used fluids. More specifically, the flow rate calibration curve data storage part 24 stores multiple gas types and pieces of flow rate calibration curve data Eq corresponding to the gas types as pairs.

The flow rate calibration curve data acquisition part 29 is configured to acquire flow rate calibration curve data Eq of fluid of a type corresponding to a fluid-specific value N calculated in the fluid-specific value calculation part 22 from the flow rate calibration curve data storage part. More specifically, the flow rate calibration curve data acquisition part 29 searches for a gas type related to a value corresponding to or closest to the calculated fluid-specific value N among the pieces of preliminarily stored correspondence relation data between the gas types and the corresponding fluid-specific values N. Then, the flow rate calibration curve data acquisition part 29 acquires flow rate calibration curve data Eq corresponding to the searched gas type from the flow rate calibration curve data storage part 24.

Even in such a configuration, even in the case where a gas type flowing through the flow path is changed, flow rate calibration curve data Eq corresponding to a new gas type is set, and in the flow rate conversion part 25, a conversion from a sensor output calculated value to a flow rate is accurately performed.

That is, the first embodiment appropriately calculates a conversion factor CF by utilizing the characteristic that a fluid-specific value N is a quantity corresponding to thermal resistivity on a one-to-one basis, and corrects a flow rate error, whereas the third embodiment is adapted to specify a gas type by utilizing the characteristic that a fluid-specific value N is a value specific to each gas, then make flow rate calibration curve data Eq corresponding to the gas type to be used, and thereby constantly output an accurate flow rate. A configuration like that of the third embodiment makes it possible to increase the output accuracy of a flow rate regardless of a gas type while decreasing an operating load because it is not necessary to calculate a conversion factor CF every time a gas type is switched.

Next, a fluid analysis device 101 in a fourth embodiment will be described with reference to FIGS. 9(*a*) and 9(*b*). Note that in the fourth embodiment, members corresponding to those in the first embodiment are denoted by the same reference signs.

The fluid analysis device 101 in the fourth embodiment does not output a flow rate, but is, as in the first embodiment, common in that voltages applied in order to make an upstream side electrical resistive element Ru and a downstream side electrical resistive element Rd generate heat are used to calculate a fluid-specific value N.

Figure 9A:
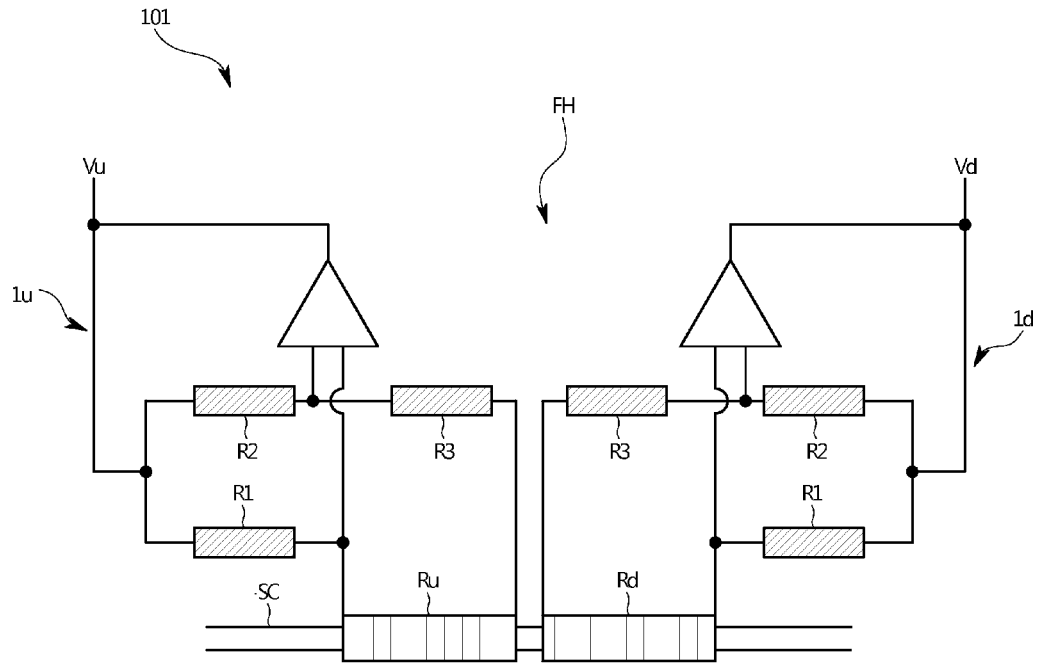
FIGS. 9(a) and 9(b) are schematic diagrams illustrating a fluid analysis device according to a fourth embodiment of the present invention.
Figure 9B:
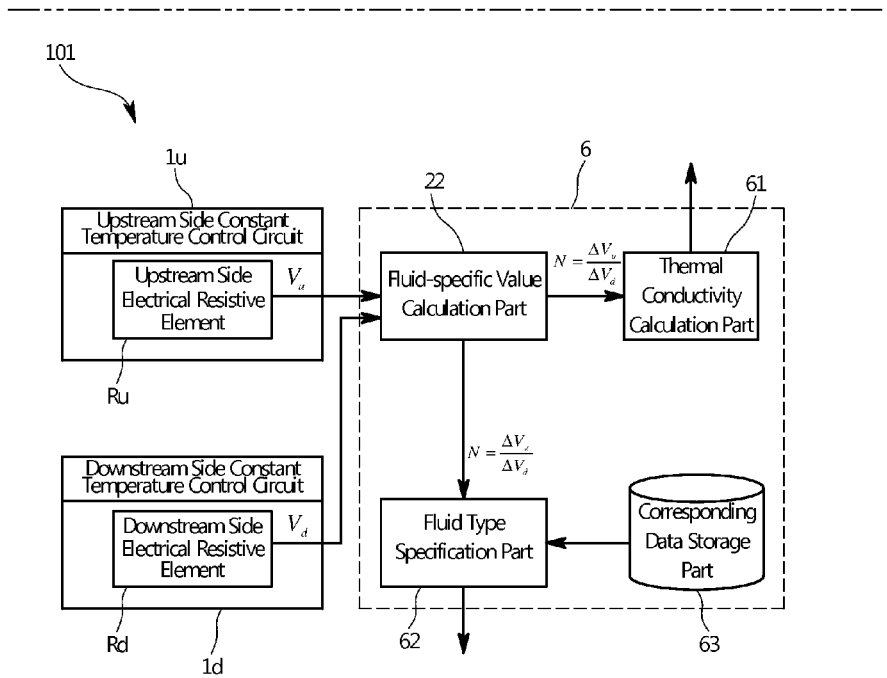

That is, as illustrated in FIG. 9(*a*), the fluid analysis device 101 is configured to include: a fluid heating part FH including the upstream side electrical resistive element Ru and downstream side electrical resistive elements Rd wound on a tube forming a flow path; and a specification part 6 that performs specification on the basis of an upstream side voltage Vu and a downstream side voltage Vd applied in order to make the upstream side electrical resistive element Ru and the downstream side electrical resistive element Rd in the fluid heating part FH.

In the fluid heating part FH, as in the thermal flowmeter 100 in the first embodiment, constant temperature control circuits that perform control so as to keep the temperatures of the upstream side electrical resistive element Ru and the downstream side electrical resistive element Rd constant are configured. The configurations and actions of the constant temperature control circuits are the same as those in the first embodiment, and therefore description thereof is omitted.

The specification part 6 (fluid analysis part) is one of which functions are realized by a so-called computer or the like, and configured to, on the basis of an upstream side parameter ΔVu and a downstream side parameter ΔVd outputted from the fluid heating part FH, calculate the fluid-specific value N exhibiting a specific value depending on the thermal conductivity of fluid, and specify the type or physical property of the measuring target fluid on the basis of the fluid-specific value N. Also, as illustrated in a functional block diagram of FIG. 9(*b*), the specification part 6 is configured to fulfill functions as at least a fluid-specific value calculation part 22, thermal conductivity calculation part 61, corresponding data storage part 63, and fluid type specification part 62.

The fluid-specific value calculation part 22 is one that as in the first embodiment, calculates the fluid-specific value N on the basis of a ratio between the upstream side parameter ΔVu and the downstream side parameter ΔVd.

The thermal conductivity calculation part 61 is one that on the basis of a linear expression representing the relationship between a fluid-specific value N and thermal conductivity, calculates thermal conductivity corresponding to the fluid-specific value N calculated in the fluid-specific calculation part 22. The linear expression is identified from the results of actually measuring fluid-specific values N on multiple types of fluids of which thermal conductivities are known.

The corresponding data storage part 63 is a database that is configured to store corresponding data including a fluid type and a fluid-specific value N of the fluid type as a pair.

The fluid type specification part 62 is one that searches the corresponding data storage part 63 for a fluid type corresponding to or close to the fluid-specific value N calculated in the fluid-specific value calculation part 22, and outputs the searched fluid type.

As described, the fluid analysis device 101 in the fourth embodiment can utilize the characteristic of the fluid-specific value N, which have been found by the present inventors, to measure the thermal conductivity of fluid or specify the type of fluid.

Other embodiments will be described.

In each of the above-described embodiments, the fluid-specific value is calculated on the basis of the upstream side voltage, downstream side voltage, upstream side parameter, and downstream side parameter obtained on the basis of the constant temperature type that applies voltages so as to keep the temperatures of the upstream side electrical resistive element and the downstream side electrical resistive element constant, but may be calculated on the basis of an upstream side voltage, a downstream side voltage, an upstream side parameter, and a downstream side parameter obtained, for example, when applying voltages on the basis of a constant current type. Also, the upstream side voltage Vu and the downstream side voltage Vd exhibits the same values, respectively, when fluid does not flow in a standard state such as a state at an ambient temperature of 25° C., but as temperature increases, may separate. In such a state, for example, in the case of the upstream side parameter ΔVu and the downstream side parameter ΔVd as illustrated in FIG. 3, a value of the fluid-specific value N changes depending on an ambient temperature. In order to make it possible to calculate the fluid-specific value N as a substantially constant value for each fluid without the effect of ambient temperature as described, it is only necessary to make a correction so as to make the upstream side voltage Vu and the downstream side voltage Vd in the state where fluid does not flow equal to values in the standard state, and on the basis of a corrected upstream side parameter ΔVu+α and a corrected downstream side parameter ΔVd+β, calculate the fluid-specific value N. α and β may be defined as, for example, functions of ambient temperature, respectively. More specifically, it is only necessary to enable α and β to be defined as linear functions of a temperature index such as (Vu+Vd) correlated with an ambient temperature or a fluid temperature, and the upstream side parameter and the downstream side parameter to be appropriately corrected.

Also, the present invention is not limited to the constant temperature type or the constant current type, but may be adapted to calculate the fluid-specific value on the basis of an upstream side voltage, a downstream side voltage, an upstream side parameter, and a downstream side parameter obtained on the basis of a constant temperature difference type that applies voltages so as to keep the temperature difference between the upstream side electrical resistive element and the downstream side electrical resistive element constant.

In the above-described second embodiment, the fluid-specific value is used in order to monitor the concentration of mixed gas; however, the fluid-specific value may be used in order to, when purging residual measuring target gas with purge gas in order to switch a gas type, check whether or not residual gas is present. That is, a thermal flowmeter or a mass flow controller including a purge determination part that when a fluid-specific value calculated by the fluid-specific value calculation part becomes the same value as a fluid-specific value of the purge gas, determines that the purge has been just completed is also possible.

Also, concentration monitoring, thermal conductivity measurement, fluid type determination, or the like is not necessarily performed together with flow rate measurement, but may be configured as a concentration meter, thermal conductivity meter, a gas type determination device, using the fluid-specific value. Since a physical property or the like of fluid can be specified in a non-contact manner by measurement using the fluid-specific value, for example, the concentration or the like of gas in a fuel cell can be preferably measured. It is also possible to, with use of a program storage medium that is configured to store a program for instructing a computer to fulfill a function as the thermal flowmeter or fluid analysis device of the present invention, install the program in an existing device to realize the function. As the program storage medium, various medium such as a CD, DVD, HDD, and flash memory may be used.

Besides, various modifications and combinations of the embodiments may be made without departing from the scope of the present invention.

INDUSTRIAL APPLICABILITY

By using the present invention, a highly functional thermal flowmeter that can specify a fluid type using only the configuration of the thermal flowmeter, and automatically calculate a parameter specific to the fluid type, such as a conversion factor or flow rate calibration curve data can be provided. Such a thermal flow meter can accurately measure and control a flow rate of gas in, for example, a semiconductor manufacturing process or the like, making it possible to manufacture products with high accuracy.

The invention claimed is:
1. A fluid analysis device comprising:
a flow path through which measuring target fluid flows;
an upstream side electrical resistive element provided on an upstream side of the flow path;
a downstream side electrical resistive element provided on a downstream side of the flow path; and
a fluid-specific value calculation part that is configured to calculate a fluid-specific value on a basis of an upstream side parameter and a downstream side parameter, wherein
the fluid specific value exhibits a specific value depending on thermal conductivity of the fluid;
an upstream side parameter is a value related to a change rate of an upstream side voltage when a flow rate of the measuring target fluid changes;
the upstream side voltage is a voltage applied in order to make the upstream side electrical resistive element generate heat;
a downstream side parameter is a value related to a change rate of a downstream side voltage when the flow rate of the measuring target fluid changes; and
the downstream side voltage is a voltage applied in order to make the downstream side electrical resistive element generate heat.

2. A thermal flowmeter that measures the flow rate of the measuring target fluid as the fluid analysis device according to claim 1, the thermal flowmeter comprising
a flow rate calculation part that is configured to calculate the flow rate of the measuring target fluid on a basis of the upstream side voltage, the downstream side voltage, and the fluid-specific value calculated in the fluid-specific value calculation part.

3. The thermal flowmeter according to claim 2, wherein
the upstream side voltage is applied so as to make temperature of the upstream side electrical resistive element constant;
the downstream side voltage is applied so as to make temperature of the downstream side electrical resistive element constant; and
the fluid-specific value is a ratio between the upstream side parameter and the downstream side parameter.

4. The thermal flowmeter according to claim 2, wherein the flow rate calculation part includes:
the fluid-specific value calculation part;
a sensor output calculated value calculation part that is configured to calculate a sensor output calculated value on a basis of the upstream side voltage, the downstream side voltage, and a predetermined sensor output calculated value calculation expression;
a flow rate calibration curve data storage part that is configured to store flow rate calibration curve data on one reference fluid, the flow rate calibration curve data indicating a relationship between a sensor output calculated value and a flow rate;
a CF calculation part that is configured to calculate a conversion factor of the measuring target fluid on a basis of the fluid-specific value; and
a flow rate conversion part that is configured to convert the sensor output calculated value calculated in the sensor output calculated value calculation part into the flow rate of the measuring target fluid on a basis of the flow rate calibration curve data on the reference fluid and the conversion factor of the measuring target fluid.

5. The thermal flowmeter according to claim 4, wherein
the CF calculation part is configured to calculate a CF change ratio on a basis of the fluid-specific value and to calculate the conversion factor at each flow rate of the measuring target fluid from a linear expression of the flow rate:
the CF change ratio is a change ratio of the conversion factor against the flow rate of the reference fluid; and
the linear expression of the flow rate uses the CF change ratio as a slope.

6. The thermal flowmeter according to claim 2, wherein the flow rate calculation part comprises:
the fluid-specific value calculation part;
a sensor output calculated value calculation part that is configured to calculate a sensor output calculated value on a basis of the upstream side voltage, the downstream side voltage, and a predetermined sensor output calculated value calculation expression;
a flow rate calibration curve data storage part that is configured to store flow rate calibration curve data for each of thermal conductivities of multiple fluids, the flow rate calibration curve data indicating a relationship between a sensor output calculated value and a flow rate;
a flow rate calibration curve data acquisition part that is configured to acquire flow rate calibration curve data on the fluid of a type corresponding to the fluid-specific value calculated in the fluid-specific value calculation from the flow rate calibration curve data storage part; and
a flow rate conversion part that is configured to calculate the flow rate of the measuring target fluid on a basis of the flow rate calibration curve data acquired in the flow rate calibration curve data acquisition part, and the sensor output calculated value calculated in the sensor output calculated value calculation part.

7. The thermal flowmeter according to claim 2, wherein the measuring target fluid is fluid in which a first fluid and a second fluid are mixed with a predetermined mixing ratio, the thermal flowmeter further comprising:
a mixing ratio calibration curve data storage part that is configured to store mixing ratio calibration curve data indicating a relationship between a mixing ratio between the first fluid and the second fluid and a fluid-specific value of the measuring target fluid; and
a mixing ratio calculation part that is configured to calculate the mixing ratio from the fluid-specific value of the measuring target fluid and the mixing ratio calibration curve data, and
the fluid-specific value is calculated in the fluid-specific value calculation part.

8. The thermal flowmeter according to claim 7, further comprising a mixed fluid CF calculation part that is configured to calculate a conversion factor of the measuring target fluid on a basis of the mixing ratio calculated in the mixing ration calculation part.

9. A mass flow controller comprising:
the thermal flowmeter according to claim 2;
a valve for controlling the flow rate of the measuring target fluid; and
a valve control part that controls an opening level of the valve on a basis of a deviation between a measured flow rate value measured by the thermal flowmeter and a predetermined setting flow rate, and a control coefficient, wherein
the valve control part is configured to change the control coefficient, depending on the fluid-specific value calculated in the fluid-specific value calculation part.

10. A fluid property specification device that specifies a type or a physical property of the measuring target fluid as the fluid analysis device according to claim 1,
the fluid property specification device being configured as a specification part that specifies the type or the physical property of the measuring target fluid on a basis of the fluid-specific value calculated in the fluid-specific value calculation part.

11. A non-volatile recording medium that stores a program for a fluid analysis device, the program being used for a fluid analysis device comprising: a flow path through which measuring target fluid flows; an upstream side electrical resistive element provided on an upstream side of the flow path; and a downstream side electrical resistive element provided on a downstream side of the flow path,
the program instructing a computer to fulfill a function as a fluid-specific value calculation part that is configured to calculate a fluid-specific value on a basis of an upstream side parameter and a downstream side parameter, wherein
the fluid specific value exhibits a specific value depending on thermal conductivity of the fluid;
an upstream side parameter is a value related to a change rate of an upstream side voltage when a flow rate of the measuring target fluid changes;

the upstream side voltage is a voltage applied in order to make the upstream side electrical resistive element generate heat;
a downstream side parameter is a value related to a change rate of a downstream side voltage when the flow rate of the measuring target fluid changes; and
the downstream side voltage is a voltage applied in order to make the downstream side electrical resistive element generate heat.

* * * * *